United States Patent [19]

Thieme et al.

[11] Patent Number: 4,619,929

[45] Date of Patent: * Oct. 28, 1986

[54] PHENYLPIPERAZINE DERIVATIVES OF HETARYLPHENOLS AND HETARYLANILINES, THEIR PREPARATION, AND THERAPEUTIC AGENTS CONTAINING THESE COMPOUNDS

[75] Inventors: Peter C. Thieme, Wachenheim; Gerd Steiner, Kirchheim; Wolfgang Rohr, Wachenheim; Dieter Lenke, Ludwigshafen; Josef Gries, Wachenheim; Harald Weifenbach; Hans-Juergen Teschendorf, both of Ludwigshafen; Hans P. Hofmann, Limburgerhof; Horst Kreiskott, Wachenheim, all of Fed. Rep. of Germany

[73] Assignee: BASF Aktiengesellschaft, Ludwigshafen, Fed. Rep. of Germany

[*] Notice: The portion of the term of this patent subsequent to Oct. 12, 1999 has been disclaimed.

[21] Appl. No.: 590,746

[22] Filed: Mar. 19, 1984

Related U.S. Application Data

[63] Continuation of Ser. No. 339,507, Jan. 15, 1982, abandoned.

[30] Foreign Application Priority Data

Jan. 19, 1981 [DE] Fed. Rep. of Germany ....... 3101502

[51] Int. Cl.$^4$ ................ C07D 413/12; C07D 403/12; C07D 417/12; A61K 31/495
[52] U.S. Cl. ................................... 514/252; 544/366; 544/367; 544/370; 544/371
[58] Field of Search .............. 544/366, 367, 370, 371; 424/250; 514/252

[56] References Cited

U.S. PATENT DOCUMENTS

| | | | |
|---|---|---|---|
| 3,937,708 | 2/1976 | Mentrup et al. | 544/370 |
| 3,941,789 | 3/1976 | Renth et al. | 544/367 |
| 4,353,904 | 10/1982 | Thieme et al. | 424/250 |
| 4,428,950 | 1/1984 | Franke et al. | 544/371 |

Primary Examiner—George F. Lesmes
Assistant Examiner—S. A. Gibson
Attorney, Agent, or Firm—Keil & Weinkauf

[57] ABSTRACT

Novel phenylpiperazinylpropane and -butane derivatives of hetarylphenols and hetarylanilines of the formula

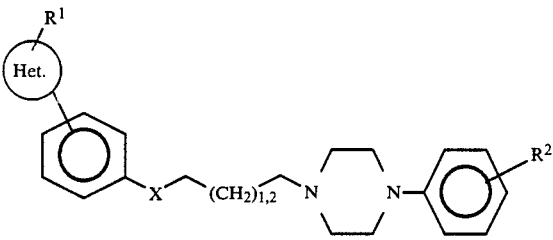

where $R^1$ is hydrogen or alkyl of 1 to 4 carbon atoms, $R^2$ is hydrogen, halogen, alkyl of 1 to 4 carbon atoms or alkoxy where alkyl is of 1 to 3 carbon atoms, the phenyl ring can be monosubstituted or disubstituted by $R^2$, X is oxygen or an NH group, and the heterocyclic structure Het. is 1,3,4-oxadiazolyl, triazolyl, imidazolyl or pyrazolyl, and their physiologically tolerated addition salts with acids, processes for their preparation, and pharmaceutical formulations which contain these compounds and exhibit predominantly sedative, neuroleptic and hypotensive properties.

10 Claims, No Drawings

PHENYLPIPERAZINE DERIVATIVES OF HETARYLPHENOLS AND HETARYLANILINES, THEIR PREPARATION, AND THERAPEUTIC AGENTS CONTAINING THESE COMPOUNDS

This is a continuation of application Ser. No. 339,507 filed Jan. 15, 1982, which application has now been abandoned.

The present invention relates to novel phenylpiperazinylpropane derivatives of hetarylphenols and hetarylanilines and their physiologically tolerated addition salts with acids, processes for their preparation and pharmaceutical formulations which contain these compounds and exhibit predominantly sedative, neuroleptic and hypotensive properties.

Patent Application No. P 30 05 287.0 describes (1,3,4-oxadiazolylphenoxy)-(phenylpiperazinyl)-propanols which exhibit a hypotensive action. This Application relates to derivatives modified by altering the side chain and, in some cases, the heterocyclic ring, which exhibit a different profile of pharmacological action.

We have found that compounds of the general formula I

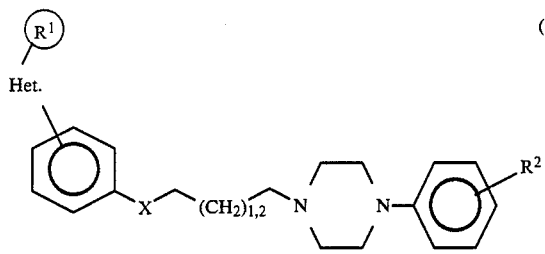

where $R^1$ is hydrogen or alkyl of 1 to 4 carbon atoms, $R^2$ is hydrogen, halogen, alkyl of 1 to 4 carbon atoms or alkoxy where alkyl is of 1 to 3 carbon atoms, the phenyl ring can be monosubstituted or disubstituted by $R^2$, X is oxygen or an NH group, and the heterocyclic structure Het. is 1,3,4-oxadiazolyl, triazolyl, imidazolyl or pyrazolyl, and their addition salts with acids exhibit useful pharmacological properties.

The heterocyclic structure can be in the o-, m- or p-position with respect to the ether group or amino group.

Methyl, ethyl, n-propyl, isopropyl, n-butyl and tert.-butyl are examples of straight-chain or branched alkyl $R^1$ of 1 to 4 carbon atoms. $R^1$ is preferably hydrogen or methyl.

$R^2$ can be in the o-, m- or p-position with respect to the piperazine substituent in the phenyl ring of the phenylpiperazine, and can have, for example, the following meanings: fluorine, chlorine, bromine and iodine are suitable halogen atoms, and fluorine and chlorine in the p- or m-position are preferred. Methoxy, ethoxy, propoxy and isopropoxy are examples of lower alkoxy, and methoxy and ethoxy in the o-position are preferred.

Accordingly, the following are examples of novel compounds of the formula I: 1-[2-(1,3,4-oxadiazol-2-yl)-phenoxy]-3-[4-(4-fluorophenyl)-piperazin-1-yl]-propane, 1-[2-(1,3,4-oxadiazol-2-yl)-phenoxy]-3-[4-(2-methoxyphenyl)-piperazin-1-yl]-propane, 1-[2-(5-methyl-1,3,4-oxadiazol-2-yl)-phenoxy]-3-[4-(2-methoxyphenyl)-piperazin-1-yl]-propane, 1-[2-(5-methyl-1,3,4-oxadiazol-2-yl)-phenoxy]-3-[4-(3-methoxyphenyl)-piperazin-1-yl]-propane, 1-[2-(1,3,4-oxadiazol-2-yl)-phenoxy]-3-[4-(3-methoxyphenyl)-piperazin-1-yl]-propane, 1-[2-(1,3,4-Oxadiazol-2-yl)-phenoxy]-4-[4-(4-fluorophenyl)-piperazin-1-yl]-butane, 1-[3-(1,3,4-oxadiazol-2-yl)-phenoxy]-3-[4-(2-methoxyphenyl)-piperazin-1-yl]-propane, 1-[3-(5-methyl-1,3,4-oxadiazol-2-yl)-phenoxy]- 3-[4-(2-methoxyphenyl)-piperazin-1-yl]-propane, 1-[3-(5-methyl-1,3,4-oxadiazol-2-yl)-phenoxy]-3-[4-(3-methoxyphenyl)-piperazin-1-yl]-propane, 1-[3-(1,3,4-oxadiazol-2-yl)-phenoxy]-3-[4-(4-fluorophenyl)-piperazin-1-yl]-propane, 1-[3-(1,3,4-oxadiazol-2-yl)-phenoxy]-3-[4-(3-chlorophenyl)-piperazin-1-yl]-propane, 1-[3-(5-methyl-1,3,4-oxadiazol-2-yl)-phenoxy]-3-[4-(2-chlorophenyl)-piperazin-1-yl]-propane, 1-[3-(5-methyl-1,3,4-oxadiazol-2-yl)-phenoxy]-4-[4-(2-methoxyphenyl)-piperazin-1-yl]-butane, 1-[3-(5-methyl-1,3,4-oxadiazol-2-yl)-phenoxy]-4-[4-(4-fluorophenyl)-piperazin-1-yl]-butane, 1-[4-(1,2,4-triazol-1-yl)-phenoxy]-3-[4-(4-fluorophenyl)-piperazin-1-yl]-propane, 1-[4-(imidazol-1-yl)-phenoxy]-3-[4-(4-fluorophenyl)-piperazin-1-yl]-propane, 1-[4-(pyrazol-1-yl)-phenoxy]-3-[4-(4-fluorophenyl)-piperazin-1-yl]-propane, 1-[4-(1,3,4-oxadiazol-2-yl)-phenoxy]-3-[4-(2-methoxyphenyl)-piperazin-1-yl]-propane, 1-[4-(1,3,4-oxadiazol-2-yl)-phenoxy]-3-[4-(4-fluorophenyl)-piperazin-1-yl]-propane, 1-[4-(1,2,4-triazol-1-yl)-phenylamino]-3-[4-(4-fluorophenyl)-piperazin-1-yl]-propane and 1-[4-(imidazol-1-yl)-phenylamino]-3-[4-(4-fluorophenyl)-piperazin-1-yl]-propane.

Compounds of the general formula I as claimed in claim 1, where $R^1$ is hydrogen or methyl, $R^2$ is fluorine, chlorine or methoxy, X is oxygen or an NH group, and the heterocyclic structure Het. is in the m- or p-position, and their physiologically tolerated addition salts with acids are particularly preferred.

The following compounds are particularly preferred and effective: 1-[4-(1,2,4-triazol-1-yl)-phenoxy]-3-[4-(4-fluorophenyl)-piperazin-1-yl]-propane 1-[4-(imidazol-1-yl)-phenoxy]-3-[4-(4-fluorophenyl)-piperazin-1-yl]-propane, 1-[4-(1,2,4-triazol-1-yl)-phenylamino]-3[4-(4-fluorophenyl)-piperazin-1-yl]-propane, 1-[4-(imidazol-1-yl)-phenylamino]-3-[4-(4-fluorophenyl)-piperazin-1-yl]-propane, 1-[4-(1,3,4-oxadiazol-2-yl)-phenoxy]-3-[4-(2-methoxyphenyl)-piperazin-1-yl]-propane, 1-[4-(1,3,4-oxadiazol-2-yl)-phenoxy]-3-[4-(4-fluorophenyl)-piperazin-1-yl]-propane, 1-[3-(1,3,4-oxadiazol-2-yl)-phenoxy]-3-[4-(2-methoxyphenyl)-piperazin-1-yl]-propane, 1-[3-(5-methyl-1,3,4-oxadiazol-2-yl)-phenoxy]-3-[4-(2-methoxyphenyl)-piperazin-1-yl]-propane, 1-[3-(1,3,4-oxadiazol-2-yl)-phenoxy]-3-[4-(4-fluorophenyl)-piperazin-1-yl]-propane and 1-[3-(5-methyl-1,3,4-oxadiazol-2-yl)-phenoxy]-4-[4-(2-methoxyphenyl)-piperazin-1-yl]-butane.

The novel compounds are obtained when an alkylated hetarylphenol or hetarylaniline of the general formula II

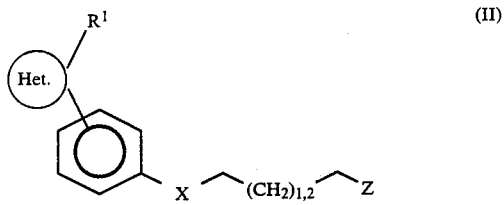

where $R^1$ and X have the meanings given for formula I and Z is halogen, in particular chlorine or bromine, or another nucleofugic leaving group, e.g. tosyloxy, is reacted in a conventional manner with a phenylpiperazine of the general formula III

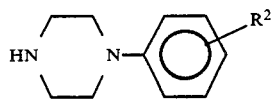

where $R^2$ has the meanings given for formula I, advantageously in a solvent and in the presence or absence of an acid acceptor, and the resulting compound is converted, if appropriate, into the addition salt of a physiologically tolerated acid.

The reactions are carried out at from 10° to 120° C., advantageously at from 50° to 120° C., under atmospheric pressure, or under superatmospheric pressure in a closed vessel, with or without heating to the above temperature range.

The reactions are advantageously carried out in the presence of an inert diluent or solvent, for example a lower alcohol of 1 to 4 carbon atoms, e.g. methanol, ethanol or propanol, preferably isopropanol or ethanol, a lower saturated dialkyl ether, dialkyl glycol ether or cyclic ether, e.g. diethyl ether, 1,2-dimethoxyethane, tetrahydrofuran or dioxane, an aromatic hydrocarbon, such as benzene or an alkylbenzene, e.g. toluene or xylene, a saturated aliphatic hydrocarbon, e.g. hexane, heptane or octane, a lower aliphatic ketone, e.g. acetone, methyl ethyl ketone or methyl isobutyl ketone, a dialkylformamide, e.g. dimethylformamide or diethylformamide, or dimethylsulfoxide, or in the presence of water, or in mixtures of the above solvents.

The reaction of a compound of the formula II with a phenylpiperazine of the formula III is preferably carried out using a lower alcohol, in particular ethanol or isopropanol, or dimethylsulfoxide as the solvent, and preferably at from 50° to 120° C. and under atmospheric pressure. The reaction is carried out in the presence or absence of a catalytic amount of sodium iodide or potassium iodide.

In an advantageous embodiment of the nucleophilic substitution of Z, the reaction is carried out in the presence of a base as the acid acceptor. Preferred bases are alkali metal hydroxides, carbonates, bicarbonates or alcoholates, tertiary organic amines, e.g. pyridine, or trialkylamines, e.g. trimethylamine or triethylamine. Particularly suitable alkali metal compounds are those of sodium and potassium. The base is used in a stoichiometric amount or in slight excess. The phenylpiperazine derivative employed for the reaction may also advantageously be used, in excess, as the acid acceptor.

The overall reaction is complete in general in the course of from 2 to 15 hours, depending on the reaction temperature. The product can be obtained in a conventional manner, for example by filtration or by distilling off the diluent or solvent from the reaction mixture, and can be purified in a conventional manner, for example by recrystallization from a solvent, conversion to an addition compound with an acid, or column chromatography.

The alkylated hetarylphenols or hetarylanilines of the general formula II are obtained when a hetarylphenol or hetarylaniline of the general formula IV

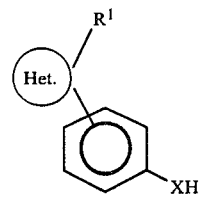

where $R^1$ and X have the meanings given for formula I, is reacted with an $\alpha,\omega$-dihalopropane or $\alpha,\omega$-dihalobutane, preferably an $\alpha$-chloro-$\omega$-bromo- mixed derivative, according to the following equation:

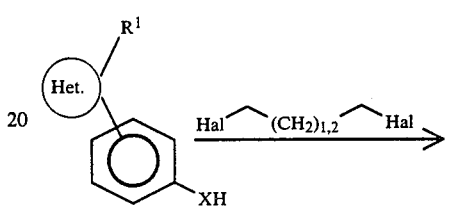

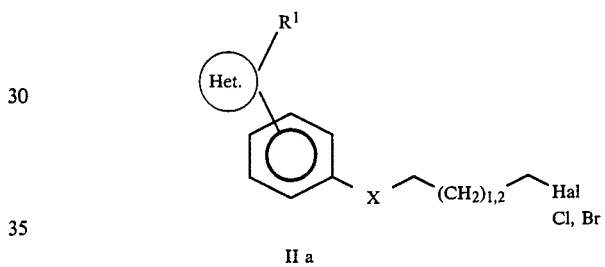

The reactions are advantageously carried out at from 0° to 120° C., under atmospheric pressure, or under superatmospheric pressure in a closed vessel, and are in general complete in the course of from 2 to 15 hours. They are advantageously carried out in an inert diluent or solvent, for example a saturated aliphatic or cyclic ether, e.g. dialkyl ether or a solvent such as dimethylsulfoxide. The reactions are preferably carried out in the presence of a base as the acid acceptor. Suitable bases are alkali metal carbonates, bicarbonates, hydroxides, hydrides or alcoholates, in particular sodium hydride. The base can be used in a catalytic or stoichiometric amount or in slight excess, based on the alkylating agent employed.

A compound of the formula I can also be obtained when a hetarylphenol or hetarylaniline of the formula IV is reacted with an phenylpiperazinyl-w-haloalkane of the general formula V.

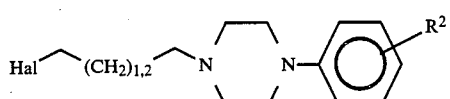

where $R^2$ has the meanings given for formula I and Hal is halogen.

The reactions are advantageously carried out at from room temperature to 100° C. in an inert solvent, for example a lower aliphatic ketone, e.g. acetone, methyl ethyl ketone or methyl isobutyl ketone, in the presence of a weak base, preferably an alkali metal carbonate, with the addition of a catalytic amount of potassium iodide, or in a polar aprotic solvent, preferably dimethylformamide, in the presence of a strong base, preferably an alkali metal hydride.

The overall reaction is complete in general in the course of from 3 to 40 hours, depending on the reaction temperature. The product can be obtained in a conventional manner, for example by filtration or by distilling off the diluent or solvent from the reaction mixture, and can be purified in a conventional manner, for example by recrystallization from a solvent, conversion to an addition compound with an acid, or column chromatography.

The phenylpiperazinyl-w-haloalkane derivatives of the formula V are known from the literature and can be prepared, as described in the Examples, by alkylating the phenylpiperazine with an α,ω-dihalopropane or α,ω-dihalobutane, preferably a chlorine/bromine mixed derivative, in the presence of a base as the acid acceptor, in an inert solvent.

The hetarylphenols or hetarylanilines employed as starting compounds of the formula IV are known from the literature (German Laid-Open Applications DOS Nos. 2,811,638, DOS 2,803,870 and DOS 2,510,781; J. med. pharm. Chem. 5 (1962), 383-389; and Bull. Soc. Chim. Fr. (1976), 839-844) and are also described in Patent Application P No. 30 05 287.0.

The novel compounds obtained may be converted into the addition salt of a physiologically tolerated acid. Examples of customary physiologically tolerated inorganic acids are hydrochloric acid, hydrobromic acid, phosphoric acid or sulfuric acid, and examples of organic acids are oxalic acid, maleic acid, fumaric acid, lactic acid, tartaric acid, malic acid, citric acid, salicylic acid, adipic acid or benzoic acid, or others which are described in Fortschritte der Arzneimittelforschung Volume 10 (1966), 224-225, Birkhäuser Verlag, Basel and Stuttgart.

As a rule, the addition salts with acids are obtained in a conventional manner by mixing the free base, or a solution thereof, with the appropriate acid, or a solution thereof, in an organic solvent, for example a lower alcohol, e.g. methanol, ethanol or propanol, a lower ketone, e.g. acetone, methyl ethyl ketone or methyl isobutyl ketone, or an ether, e.g. diethyl ether, tetrahydrofuran or dioxane. To facilitate the precipitation of crystals, mixtures of the above solvents can also be used. It is also possible to prepare a pharmaceutically acceptable aqueous solution of an addition compound of a phenylpiperazinyl derivative of the general formula (I) with an acid, by dissolving the free base of the general formula (I) in an aqueous solution of an acid.

The novel compounds and their physiologically tolerated addition salts with acids are useful as drugs having a hypotensive, sedative and neuroleptic action.

The pharmacological actions were demonstrated using the following methods:

Hypotensive action

The hypotensive action was demonstrated on Sprague-Dawley rats (weight: 230-280 g) under urethane narcosis (1.78 g/kg, administered intraperitoneally). The blood pressure was measured in the carotid artery. The substance was administered either by introduction into a jugular vein (as an aqueous solution, at the rate of 1 ml/kg) or intraperitoneally as a suspension in tragacanth (at the rate of 10 ml/kg). The ED 20%, i.e. the dose which produces a 20% lowering of the blood pressure, was determined from the linear regression of log dose (mg/kg) and relative lowering of the blood pressure ($\Delta$ %).

Sedative action

The substance was administered orally to 4–8 groups each comprising 3 female NMRI mice. The orientation hypermotility induced by a new environment was determined photoelectrically, 30 minutes after administration of the substance, over a period of 30 minutes. The ED 50%, i.e. the dose which produces 50% reduction in orientation hypermotility compared to placebo-treated control animlas, is determined.

Some of the compounds claimed have an extremely powerful hypotensive action (Table 1). The compounds of Examples 1, 3, 6, 7 and 11 lower the blood pressure of narcotized rats when used in doses which, with the exception of the compound of Example 3, are significantly lower than in the case of chlorpromazine. In contrast, the difference in magnitude between the sedative action, which is to be regarded as a side effect, and the desired hypotensive action is substantially greater in the case of Examples 1, 3, 6, 7 and 11 than in the case of chlorpromazine.

The compounds of Examples 10, 14 and 15 (Table 2) exhibit powerful inhibition of the orientation hypermotility of mice, as a result of a sedative-neuroleptic action. The action of chlorpromazine is almost achieved by Example 10 and is clearly surpassed by Examples 14 and 15. In contrast to chlorpromazine, the substances have a non-hypotensive action up to doses of 1 or 10 mg/kg, and thereby differ favorably from chlorpromazine, in which the side effect, which is undesirable in sedatives or neuroleptics, is observed even at low doses.

TABLE 1

| Compound of Example No. | Hypotensive effect | | Sedative effect | | |
|---|---|---|---|---|---|
| | ED 20% 1 | R.A. 2 | ED 50% 3 | R.A. 2 | Q 4 |
| 3 | 0.0384 | 0.68 | 20.5 | 0.10 | 534 |
| 1 | 0.008 | 3.25 | 16.4 | 0.13 | 2,050 |
| 7 | 0.00120 | 2.17 | 3.74 | 0.56 | 312 |
| 6 | 0.00770 | 3.38 | 3.21 | 0.66 | 417 |
| 11 | 0.0070 | 3.71 | 2.15 | 0.98 | 307 |
| chlor-promazine | 0.0260 | 1.00 | 2.11 | 1.00 | 81 |

1 Dose which reduces the blood pressure by 20% (rat, intravenous administration)
2 Relative activity; chlorpromazine = 1.00
3 Dose which reduces the motility by 50% (mouse, oral administration)
4 $Q = \dfrac{\text{ED 50\% for sedative effect}}{\text{ED 20\% for hypotensive effect}}$

TABLE 2

| Compound of Example No. | Sedative effect 1 | | Hypotensive effect 2 | | |
|---|---|---|---|---|---|
| | ED 50% | R.A. 3 | ED 20% | R.A. 3 | Q 4 |
| 10 | 3.05 | 0.69 | 1 i.v. | 0.03 | 3.0 |
| 14 | 0.818 | 2.59 | 10 i.p. | 0.02 | 0.08 |
| 15 | 1.62 | 1.3 | 10 i.v. | 0.003 | 0.16 |
| chlor-promazine | 2.11 | 1.0 | 0.026 i.v. | 1.0 | 81.0 |
| | | | 0.164 i.p. | 1.0 | 12.9 |

1 Mouse, oral administration
2 Rat, intravenous (i.v.) or intraperitoneal (i.p.) administration
3 Relative activity; chlorpromazine = 1.00
4 $Q = \dfrac{\text{ED 50\% for sedative effect}}{\text{ED 20\% for hypotensive effect}}$ Accordingly, the present invention also relates to therapeutic agents or formulations which in addition to conventional carriers and diluents contain a compound of the formula I, or a physiologically tolerated addition salt thereof with an acid, as the active compound.

The novel compounds may be employed in the conventional solid or liquid pharmaceutical forms, such as tablets, capsules, powders, granules, coated tablets or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The preferred formulations are those suitable for oral administration. Examples of these are tablets, film tablets, coated tablets, capsules, pills, powders, solutions, suspensions and depot forms. Parenteral formulations, such as injection solutions, may also be used. Suppositories are a further example of suitable formulations.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Correspondingly, coated tablets can be prepared by coating cores, prepared similarly to the tablets, with agents conventionally used in tablet coatings, for example collidone or shellac, gum arabic, talc, titanium dioxide or sugar. The coating can also consist of a plurality of layers, and the auxiliaries mentioned above in connection with tablets may be used therein.

Solutions or suspensions containing the novel active compounds may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The dosage of the compounds according to the invention depends on the age, condition and weight of the patient and on the route of administration. As a rule, the daily dose of active compound is from 5 to 100, preferably from 10 to 80, mg.

The Examples which follow illustrate the invention.

EXAMPLE 1

1-[2-(1,3,4-Oxadiazol-2-yl)-phenoxy]-3-[4-(2-methoxyphenyl)-piperazin-1-yl-propane. H$_2$O 4.5 g (0.0167 mole) of 1-(3-chloropropyl)-4-(2-methoxyphenyl)-piperazine, 2.3 g (0.0167 mole) of potassium carbonate and a pinch of potassium iodide are added to 2.7 g (0.0167 mole) of 2-(1,3,4-oxadiazol-2-yl)-phenol in 80 ml of methyl ethyl ketone, and the mixture is refluxed for from 20 to 40 hours. The mixture is cooled, the residue is filtered off and the mother liquor is concentrated. The residue is digested with ether, filtered off under suction, washed thoroughly with ether and dried. 6.2 g (90%) of a product of melting point 132°–133° C. are obtained.

EXAMPLE 2

1-[2-(1,3,4-Oxadiazol-2-yl)-phenoxy]-3-[4-(4-fluorophenyl)-piperazin-1-yl]-propane The preparation is carried out as described in Example 1, using 1-(3-chloropropyl)-4-(4-fluorophenyl)-piperazine. The solvent is distilled off, the residue is recrystallized from toluene/petroleum ether, and colorless crystals of melting point 102°–103° C. are obtained (yield: 71%).

EXAMPLE 3

1-[2-(5-Methyl-1,3,4-oxadiazol-2-yl)-phenoxy]-3-[4-(2-methoxyphenyl)-piperazin-1-yl]-propane. H$_2$O The preparation is carried out as described in Example 1, using 2-(5-methyl-1,3,4-oxadiazol-2-yl)-phenol, and a product of melting point 99°–100° C. is obtained (yield: 57%).

EXAMPLE 4

1-[2-(5-Methyl-1,3,4-oxadiazol-2-yl)-phenoxy]-3-[4-(3-methoxyphenyl)-piperazin-1-yl]-propane . 2HCl . ½ H$_2$O The preparation is carried out as described in Example 1, using 2-(5-methyl-1,3,4-oxadiazol-2-yl)-phenol and 1-(3-chloropropyl)-4-(3-methoxyphenyl)-piperazine. The mother liquor is concentrated, the residue is dissolved in methylene chloride/ether, and the hydrochloride is precipitated using ethereal hydrochloric acid. A product of melting point 147°–148° C. is obtained (yield: 56%).

EXAMPLE 5

1-[2-(1,3,4-Oxadiazol-2-yl)-phenoxy]-3-[4-(3-methoxyphenyl)-piperazin-1-yl]-propane. 2.5HCl . ½ H$_2$O The preparation is carried out as described in Example 1, using 1-(3-chloropropyl)-4-(3-methoxyphenyl)-piperazine. The crude product is purified by column chromatography (silica gel, mobile phase chloroform/methanol 6/1), dissolved in either, and converted into the hydrochloride using ethereal hydrochloric acid. A product of melting point 129°–130° C. is obtained (yield: 56%).

EXAMPLE 6

1-[3-(1,3,4-Oxadiazol-2-yl)-phenoxy]-3-[4-(2-methoxyphenyl)-piperazin-1-yl]-propane. 2.5HCl. H$_2$O The preparation is carried out as described in Example 1, using 3-(1,3,4-oxadiazol-2-yl)-phenol. The crude product is dissolved in methylene chloride/ether and converted into the hydrochloride using ethereal hydrochloric acid, and the hydrochloride can then be recrystallized from ethanol/dimethylformamide/ether to give a product of melting point 248°–249° C. (yield: 25%).

EXAMPLE 7

1-[3-(5-Methyl-1,3,4-oxadiazol-2-yl)-phenoxy]-3-[4-(2-methoxyphenyl)-piperazin-1-yl]-propane. 2HCl . ½ H$_2$O The preparation is carried out as described in Example 1, using 3-(5-methyl-1,3,4-oxadiazol-2-yl)-phenol. The crude product is dissolved in methylene chloride/ether and converted into the hydrochloride using ethereal hydrochloric acid. A product of melting point 224°–225° C. is obtained (yield: 84%).

EXAMPLE 8

1-[3-(5-Methyl-1,3,4-oxadiazol-2-yl)-phenoxy]-3-[4-(3-methoxyphenyl)-piperazin-1-yl]-propane. 2.5HCl. $H_2O$ The preparation is carried out as described in Example 1, using 3-(5-methyl-1,3,4-oxadiazol-2-yl)-phenol and 1-(3-chloropropyl)-4-(3-methoxyphenyl)-piperazine. The crude product is dissolved in methylene chloride/ether and converted into the hydrochloride using ethereal hydrochloric acid. The crude hydrochloride is digested in water and filtered off from the insoluble residue, and the filtrate is rendered alkaline. The purified free base is isolated by extraction with methylene chloride and dissolved in methylene chloride/ether, the solution is filtered, and the base is again converted into the hydrochloride using ethereal hydrochloric acid. A product of melting point 148°–150° C. is obtained (yield: 28%).

EXAMPLE 9

1-[3-(1,3,4-oxadiazol-2-yl)-phenoxy]-3-[4-(4-fluorophenyl)-piperazin-1-yl]-propane The preparation is carried out as described in Example 1, using 3-(1,3,4-oxadiazol-2-yl)-phenol and 1-(3-chloropropyl)-4-(4-fluorophenyl)-piperazine. The crude product is recrystallized from toluene/petroleum ether, and a product of melting point 105°–106° C. is obtained (yield: 68%).

EXAMPLE 10

1-[4-(Imidazol-1-yl)-phenoxy]-3-4-(4-fluorophenyl)-piperazin-1-yl)-propane

The preparation is carried out as described in Example 1, using 4-(imidazol-1-yl)-phenol and 1-(3-chloropropyl)-4-(4-fluorophenyl)-piperazine. The crude product is purified by column chromatography (silica gel, mobile phase: methylene chloride) and recrystallized from ethanol. A product of melting point 150°–151° C. is obtained (yield: 35%).

EXAMPLE 11

1-[4-(1,3,4-Oxadiazol-2-yl)-phenoxy]-3-[4-(2-methoxyphenyl)-piperazin-1-yl]-propane The preparation is carried out as described in Example 1, using 4-(1,3,4-oxadiazol-2-yl)-phenol. About 10 ml of acetone are added to the filtered reaction mixture, and the resulting precipitate is filtered off under suction and washed with ether. A product of melting point 139°–140° C. is obtained (yield: 69%).

EXAMPLE 12

1-[4-(1,3,4-Oxadiazol-2-yl)-phenoxy]-3-[4-(4-fluorophenyl)-piperazin-1-yl]-propane The preparation is carried out as described in Example 1, using 4-(1,3,4-oxadiazol-2-yl)-phenol and 1-(3-chloropropyl)-4-(4-fluorophenyl)-piperazine. The crude product is recrystallized from toluene and subsequently from ethanol, and a product of melting point 157°–158° C. is obtained (yield: 66%).

EXAMPLE 13

1-[4-(Pyrazol-1-yl)-phenoxy]-3-[4-(4-fluorophenyl)-piperazin-1-yl]-propane 0.66 g (0.0152 mole) of sodium hydride (55% strength in liquid paraffin) is added to 2.1 g (0.0131 mole) of 4-(pyrazol-1-yl)-phenol in 60 ml of absolute dimethylformamide, and the mixture is stirred for 1 hour at room temperature. 3.99 g (0.0131 mole) of 1-(3-chloropropyl)-4-(4-fluorophenyl)-piperazine are added, the reaction mixture is stirred for 3 hours at 90° C., under nitrogen as a protective gas, cooled and poured onto ice water, and the precipitate is filtered off under suction. The crude product is recrystallized from ethanol and a product of melting point 151°–153° C. is obtained (yield: 72%).

EXAMPLE 14

1-[4-(1,2,4-Triazol-1-yl)-phenylamino]-3-[4-(4-fluorophenyl)-piperazin-1-yl]-propane . $H_2O$ The preparation is carried out as described in Example 13, using 4-(1,2,4-triazol-1-yl)-phenol. The reaction mixture is cooled, the solvent is distilled off under reduced pressure from an oil pump, the residue is digested in methylene chloride, the insoluble material is filtered off and the solution is purified by column chromatography (silica gel, methylene chloride/methanol 98/2 as the mobile phase). The product purified in this manner can additionally be recrystallized from ethanol, and a compound of melting point 145°–146° C. is obtained (yield: 35%).

EXAMPLE 15

1-[4-(Imidazol-1-yl)-phenylamino]-3-[4-(4-fluorophenyl)-piperazin-1-yl]-propane

The preparation is carried out as described in Example 13, using 4-(imidazol-1-yl)-phenol, and the working up is similar to that of Example 14. The product is subjected to column chromatography and recrystallized from ethanol, with the addition of active charcoal. A compound of melting point 164°–166° C. is obtained (yield: 21%).

EXAMPLE 16

Preparation of 1-(3-chloropropyl)-4-(4-fluorophenyl)-piperazine 26.1 g (0.166 mole) of 1-bromo-3-chloropropane and 33.6 g (0.333 mole) of triethylamine are added to 30.0 g (0.166 mole) of 1-(4-fluorophenyl)-piperazine in 50 ml of tetrahydrofuran. The reaction mixture is stirred for 16 hours at from 60° to 65° C., cooled and filtered, the solvent is stripped off under reduced pressure, and the crude product is distilled under reduced pressure from an oil pump. The product distils at 135°–145° C./0.05 mm Hg in a yield of 30.0 g (70%).

EXAMPLE 17

The remaining 1-(3-chloropropyl 1)-piperazines, 1-(3-chloropropyl)-4-(2-methoxyphenyl)-piperazine and 1-(3-chloropropyl)-4-(3-methoxyphenyl)-piperazine, are prepared as described in Example 16.

EXAMPLE 18

1-[3-(1,3,4-Oxadiazol-2-yl)-phenoxy]-3-[4-(3-chlorophenyl)-piperazin-1-yl]-propane. 2HCl. 1.5 $H_2O$ (a) 7.1 g (0.0377 mole) of 1-(3-chlorophenyl)-piperazine are added to 4.5 g (0.0188 mole) of 1-[3-(1,3,4- oxadiazol-2-yl)-phenoxy]-3-chloropropane in 100 ml of isopropanol, the mixture is refluxed for 26 hours and then cooled, the isopropanol phase is decanted off from the oil which separates out, and the solvent is stripped off. The residue is dissolved in methylene chloride, and the solution is washed with water, dried and again concentrated. The crude product is dissolved in methylene chloride/ether, and the hydrochloride is precipitated using ethereal hydrochloric acid and then recrystallized from isopropanol/dimethylformamide/ether. A product of melting point 209°–213° C. is obtained (yield: 12%).

(b) The intermediate 1-[3-(1,3,4-oxadiazol-2-yl)-phenoxy]-3-chloropropane is prepared in the following manner:

6.6 g (0.152 mole) of sodium hydride (55% strength in liquid paraffin) are introduced into 130 ml of absolute dimethylsulfoxide. To the mixture are added dropwise, whilst stirring, 24.4 g (0.152 mole) of 3-(1,3,4-oxadiazol-2-yl)-phenol dissolved in 100 ml of absolute dimethylsulfoxide at room temperature, followed by 59.6 g (0.379 mole) of 1-bromo-3-chloropropane. Stirring is continued for 12 hours at from 50° to 60° C., and the mixture is worked up by adding 500 ml of water and extracting with three times 150 ml of methylene chloride. The organic phase is washed with sodium carbonate solution, dried and concentrated, and the crude product is isolated, taken up in methanol to remove liquid paraffin, and then further purified by shaking it with 4N sodium hydroxide solution. The sodium hydroxide solution is decanted off, the oil is taken up with 2N hydrochloric acid, and the product is extracted with ether. The product is sufficiently pure for further reaction. Yield: 55%.

EXAMPLE 19

1-[3-(5-Methyl-1,3,4-oxadiazol-2-yl)-phenoxy]-3-[4-(2-chlorophenyl)-piperazin-1-yl]-propane 2.5HCl . ½ H$_2$O (a) The preparation is carried out as described in Example 18 a, using 1-[3-(5-methyl-1,3,4-oxadiazol-2-yl)-phenoxy]-3-chloropropane and 1-(2-chlorophenyl)-piperazine and increasing the refluxing time to 60 hours. The solvent is removed under reduced pressure, the crude product is purified by column chromatography (silica gel, mobile phase chloroform/ethyl acetate 1/1), the purified product is dissolved in ether, the solution is filtered, and the compound is converted into the hydrochloride using ethereal hydrochloric acid. A product of melting point 205°–207° C. is obtained (yield: 26%).

(b) The intermediate 1-[3-(5-methyl-1,3,4-oxadiazol-2-yl)-phenoxy]3-chloropropane is prepared as described in Example 18 b, using 3-(5-methyl-1,3,4-oxadiazol-2-yl)-phenol. Yield: 59%.

EXAMPLE 20

1-[4-(1,2,4-Triazol-1-yl)-phenoxy]-3-[4-(4-fluorophenyl)-piperazin-1-yl]-propane (a) 4.7 g (0.026 mole) of 1-(4-fluorophenyl)-piperazine are added to 3.0 (0.013 mole) of 1-[4-(1,2,4-triazol-1-yl)-phenoxy]-3-chloropropane in 50 ml of ethanol, the mixture is refluxed for 35 hours and then cooled, and the precipitate is filtered off under suction. A product of melting point 134°–135° C. is obtained (yield: 49%).

(b) The intermediate 1-[4-(1,2,4-triazol-1-yl)-phenoxy]-3-chloropropane is prepared as described in Example 18b, using 4-(1,2,4-triazol-1-yl)-phenol and stirring the mixture for 3 hours at room temperature. The mixture is then poured onto ice/water, sodium chloride is added and the product is extracted with ether. The organic phase is dried and concentrated, and the crude product obtained is taken up in methanol to remove liquid paraffin, and recrystallized from cyclohexane. A product of melting point 81°–82° C. is obtained (yield: 48%).

EXAMPLE 21

1-[2-(1,3,4-Oxadiazol-2-yl)-phenoxy]-4-4-(4-fluorophenyl)-piperazin-1-yl]-butane . 3HCl . H$_2$O (a) 3.5 g (0.0194 mole) of 1-(4-fluorophenyl)-piperazine are added to 4.9 g (0.194 mole) of 1-[2-(1,3,4-oxadiazol-2-yl)-phenoxy]-4-chlorobutane in 50 ml of dimethylsulfoxide, the mixture is stirred for 30 hours at 80° C., poured into ice/water and acidified with dilute hydrochloric acid, and the product is extracted with ether. The aqueous phase is then rendered alkaline with dilute sodium hydroxide solution and again extracted with ether. The basic ether phase is washed, dried and concentrated, the crude product obtained is purified by dissolving it in ether and converting it into the hydrochloride using ethereal hydrochloric acid, and hydrochloride is recrystallized from ethanol. A product of melting point 240°–241° C. is obtained (yield: 28%).

(b) The intermediate 1-[2-(1,3,4-oxadiazol-2-yl)-phenoxy]-4-chlorobutane is prepared in the following manner:

2.69 g (0.0618 mole) of sodium hydride (55% strength in liquid paraffin) are introduced into 100 ml of absolute dimethylsulfoxide. 10.0 g (0.0618 mole) of 2-(1,3,4-oxadiazol-2-yl)-phenol are added a little at a time, and 39.2 g (0.308 mole) of 1,4-dichlorobutane are then added dropwise at 15° C., whilst stirring. Stirring is continued for 20 hours at 50° C., the mixture is cooled, poured onto ice/water and acidified with dilute hydrochloric acid, the resulting organic lower phase is separated off and the aqueous phase is extracted with methylene chloride. The combined organic phases are freed from solvent and excess 1,4-dichlorobutane by distillation, and the crude product is recrystallized from naphtha. Yield: 37%.

EXAMPLE 22

1-[3-(5-Methyl-1,3,4-oxadiazol-2-yl)-phenoxy]-4-[4-(4-fluorophenyl)-piperazin-1-yl]-butane (a) The preparation is carried out as described in Example 21 a, using 1-[3-(5-methyl-1,3,4-oxadiazol-2-yl)-phenoxy]-4-chlorobutane and reducing the reaction time to 12 hours. The reaction mixture is cooled and left to stand for several hours at room temperature, the precipitate is filtered off under suction and washed thoroughly with ether, and the crude product is recrystallized from toluene. A product of melting point 146°–147° C. is obtained (yield: 41%).

(b) The intermediate 1-[3-(5-methyl-1,3,4-oxadiazol-2-yl)-phenoxy]-4-chlorobutane is prepared as described in Example 21 b. After the acidification step in the working-up procedure, the organic lower phase is separated off, a little methylene chloride is added, and the mixture is dried and concentrated. The precipitate produced at 0° C. is filtered off under suction and washed with petroleum ether. The product is recrystallized from naphtha (yield: 51%).

EXAMPLE 23

1-[3-(5-Methyl-1,3,4-oxadiazol-2-yl)-phenoxy]-4-[4-(2-methoxyphenyl)-piperazin-1-yl]-butane . 2HCl . ½ H₂O.

(a) The preparation is carried out as described in Example 21 a, using 1-3-(5-methyl-1,3,4-oxadiazol-2-yl)-phenoxy]-4-chlorobutane and 1-(2-methoxyphenyl)-piperazine. The compound is converted into the hydrochloride using ethereal hydrochloric acid, and a product of melting point 193°-194° C. is obtained (yield: 84%).

(b) The preparation of the intermediate 1-[3-(5-methyl-1,3,4-oxadiazol-2-yl)-phenoxy]-4-chlorobutane is described in Example 22 b.

Examples of pharmaceutical formulations:

| Examples of tablets | |
|---|---|
| 1. An active compound of formula I | 10 mg |
| Lactose | 200 mg |
| Methylcellulose | 15 mg |
| Corn starch | 50 mg |
| Talc | 11 mg |
| Magnesium stearate | 4 mg |
| 2. An active compound of formula I | 20 mg |
| Lactose | 178 mg |
| Avicel | 80 mg |
| Polywachs 6000 | 20 mg |
| Magnesium stearate | 2 mg |
| 3. An active compound of formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |

Re 3:

The active compound is moistened with a 10% strength aqueous solution of polyvinylpyrrolidone and forced through a sieve of 1.0 mm mesh size, and the granules are dried at 50° C. They are then mixed with polyethylene glycol (mean molecular weight 4,000), hydroxypropylmethylcellulose, talc and magnesium stearate, and the mixture is pressed to give tablets weighing 280 mg.

| Example of coated tablets | |
|---|---|
| 4. An active compound of formula I | 60 mg |
| Lactose | 90 mg |
| Corn starch | 60 mg |
| Polyvinylpyrrolidone | 6 mg |
| Magnesium stearate | 1 mg |

The active compound, lactose and corn starch are mixed, moistened with an 8% strength aqueous solution of the polyvinylpyrrolidone, and granulated by passing through a 1.5 mm mesh sieve. The granules are dried at 50° C. and forced through a 1.0 mm sieve. The material thus obtained is mixed with magnesium stearate and the mixture is pressed to form cores. These are coated in a conventional manner with a shell consisting essentially of sugar and talc.

| Capsule formulation | |
|---|---|
| 5. An active compound of formula I | 5 mg |
| Magnesium stearate | 2.0 mg |
| Lactose | 19.3 mg |
| Injection solution | |
| 6. An active compound of formula I | 10 mg |
| Sodium chloride | 9 mg |
| Distilled water, to make up 1.0 ml | |

We claim:

1. A compound of the formula I

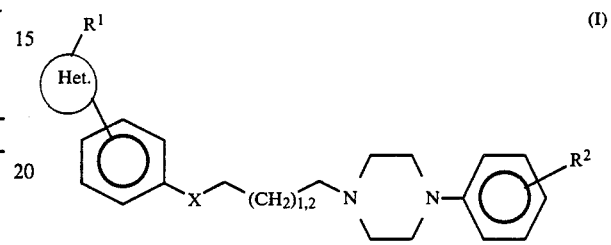

where $R^1$ is hydrogen or methyl, $R^2$ is fluorine or methoxy, X is oxygen or an NH group, and the heterocyclic structure Het. is 1,3,4-oxadiazolyl, triazolyl or imidazolyl attached in the 2-,3- or 4-position of the phenyl ring, and their physiologically tolerated addition salts with acids.

2. 1-[4-(Imidazol-1-yl)-phenoxy]-3-[4-(4-fluorophenyl-piperazin-1-yl]-propane.

3. 1-[4-(1,2,4-triazol-1-yl)-phenylamino]-3-[4-(4-fluorophenyl)-piperazin-1-yl]-propane.

4. A compound of the formula I according to claim 1, where $R^1$ is hydrogen, $R^2$ is fluorine, X is 4 NH, the index of the (CH₂)-group is one, and Het. is imidazol-1-yl in the 4-position of the phenyl-group.

5. A compound of the formula I according to claim 1, where $R^1$ is hydrogen, $R^2$ is 2-methoxy, X is oxygen, the index of the (CH₂)-group is one and Het. is 1,3,4-oxadiazol-2-yl in the 4-position of the phenyl-group.

6. A compound of the formula I according to claim 1, where $R^1$ is hydrogen, $R^2$ is 2-methoxy, X is oxygen, the index of the (CH₂)-group is one and Het. is 1,3,4-oxadiazol-2-yl in the 3-position of the phenyl-group.

7. A compound of the formula I according to claim 1, where $R^1$ is 5-methyl, $R^2$ is 2-methoxy, X is oxygen, the index of the (CH₂)-group is one and Het. is 1,3,4-oxadiazol-2-yl in the 3-position of the phenyl-group.

8. A compound of the formula I according to claim 1, where $R^1$ is 5-methyl, $R^2$ is 2-methoxy, X is oxygen, the index of the (CH₂)-group is one and Het. is 1,3,4-oxadiazol-2-yl in the 3-position of the phenyl-group.

9. A compound of the formula I according to claim 1, where $R^1$ is hydrogen, $R^2$ is 2-methoxy, X is oxygen, the index of the (CH₂)-group is one and Het. is 1,3,4-oxadiazol-2-yl in the 3-position of the phenyl-group.

10. A pharmaceutical composition in solid or liquid form having sedative, neuroleptic and hypotensive properties which comprises: a pharmaceutically acceptable diluent and from 0.001 to 99% by weight of a compound of the formula I of claim 1.

* * * * *